(12) United States Patent
Wong et al.

(10) Patent No.: US 11,484,282 B2
(45) Date of Patent: Nov. 1, 2022

(54) 3-D SCANNER CALIBRATION WITH ACTIVE DISPLAY TARGET DEVICE

(71) Applicant: Carestream Dental Technology Topco Limited, London (GB)

(72) Inventors: Victor Wong, Pittsford, NY (US); Chuanmao Fan, Rochester, NY (US)

( * ) Notice: Subject to any disclaimer, the term of this patent is extended or adjusted under 35 U.S.C. 154(b) by 0 days.

(21) Appl. No.: 16/060,853

(22) PCT Filed: Dec. 8, 2015

(86) PCT No.: PCT/US2015/064360
§ 371 (c)(1),
(2) Date: Jun. 8, 2018

(87) PCT Pub. No.: WO2017/099719
PCT Pub. Date: Jun. 15, 2017

(65) Prior Publication Data
US 2019/0000412 A1    Jan. 3, 2019

(51) Int. Cl.
*A61B 6/00* (2006.01)
*G01B 11/25* (2006.01)
*A61B 6/02* (2006.01)
*A61B 6/14* (2006.01)

(52) U.S. Cl.
CPC .............. *A61B 6/584* (2013.01); *A61B 6/022* (2013.01); *A61B 6/145* (2013.01); *G01B 11/2504* (2013.01); *G01B 11/2513* (2013.01); *G01B 11/2518* (2013.01)

(58) Field of Classification Search
CPC ......... A61B 6/022; A61B 6/145; A61B 6/584; G01B 11/2518; G01B 11/2504; G01B 11/2513
USPC ............................ 356/600–640, 239.1–239.8
See application file for complete search history.

(56) References Cited

U.S. PATENT DOCUMENTS

| | | | | |
|---|---|---|---|---|
| 5,372,502 A | * | 12/1994 | Massen | G01B 11/24 433/215 |
| 2003/0157464 A1 | * | 8/2003 | Tanassi | A61B 3/12 434/81 |
| 2005/0117696 A1 | * | 6/2005 | Suzuki | A61B 6/14 378/19 |
| 2013/0010080 A1 | * | 1/2013 | Ray | G01S 17/00 348/47 |
| 2014/0210794 A1 | * | 7/2014 | Ilmonen | G06F 3/0425 345/175 |
| 2014/0253686 A1 | * | 9/2014 | Wong | H04N 13/286 348/46 |
| 2017/0372492 A1 | * | 12/2017 | Doganis | G06T 7/70 |

* cited by examiner

*Primary Examiner* — Tri T Ton
(74) *Attorney, Agent, or Firm* — Alston & Bird LLP (57) ABSTRACT

Exemplary method and apparatus embodiments according to the applications can provide calibration of a dental scanning device. An exemplary dental apparatus can include a sensing apparatus including at least one lens and a sensor that is configured to obtain one or more images of at least one surface position, and a calibration target including a spatial light modulator configured to form a prescribed set of calibration patterns, and whose display plane corresponds to the at least one surface position.

1 Claim, 6 Drawing Sheets

3-D SCANNER CALIBRATION WITH ACTIVE DISPLAY TARGET DEVICE

TECHNICAL FIELD

The disclosure relates generally to optical scanners for surface contour characterization and more particularly to calibration targets and methods and/or apparatus for dental scanner calibration using such calibration targets.

BACKGROUND

A number of techniques have been developed for obtaining surface contour information from various types of objects in medical, industrial, and other applications. These techniques include optical 3-dimensional (3-D) measurement methods that provide shape and depth information using images obtained from patterns of light directed onto a surface.

Structured light imaging is one familiar technique that has been successfully applied for surface characterization. In structured light imaging, a pattern of illumination is projected toward the surface of an object from a given angle. The pattern can use parallel lines of light or more complex features, such as sinusoidal lines, dots, or symbols, and the like. The light pattern can be generated in a number of ways, such as using a mask, an arrangement of slits, interferometric methods, or a spatial light modulator, such as a Digital Light Processor from Texas Instruments Inc., Dallas, Tex. or similar digital micromirror device. Multiple patterns of light may be used to provide a type of encoding that helps to increase robustness of pattern detection, particularly in the presence of noise. Light reflected or scattered from the surface is then viewed from another angle as a contour image, taking advantage of triangulation in order to analyze surface information based on the appearance of contour lines or other patterned illumination.

Structured light imaging has been used effectively for surface contour imaging of solid, highly opaque objects and has been used for imaging the surface contours for some portions of the human body and for obtaining detailed data about skin structure. Recently, structured light imaging methods have been applied to the problem of dental imaging, helping to provide detailed surface information about teeth and other intraoral features. Intraoral structured light imaging is now becoming a valuable tool for the dental practitioner, who can obtain this information by scanning the patient's teeth using an inexpensive, compact intraoral scanner, such as the Model CS3500 Intraoral Scanner from Carestream Dental, Atlanta, Ga.

In order to provide accurate 3-D surface contour characterization, a contour scanning apparatus must be reasonably well calibrated. Even slight changes in adjustment resulting from continued handling or drift from factory-calibrated settings over time can adversely impact scanner performance. It can be appreciated that the capability to validate and adjust scanner calibration on-site can be beneficial for both the scanner manufacturer and the end-user.

There have been a number of tools and techniques proposed for calibration of various types of 3-D contour scanners and stereo viewing apparatus, including the following, for example: U.S. Pat. No. 7,869,026 to Boyer et al.; US Patent Application Publication No. 2005/0068523 by Wang et al.; EP 1 422 496 A1 to Otani et al. However, solutions such as those presented in the literature, while they may have achieved some level of success for device calibration in other fields, fall short of what is workable and practical for portable 3-D scanning apparatus, such as those used for intraoral imaging. Many current systems use calibration targets that require custom manufacturing. Because calibration targets require demanding accuracy specifications in attributes such as planarity, feature spacing, and feature density, they can be difficult to make and/or costly to make. Furthermore, calibration targets with a fixed shape and/or fixed markings provide only a specific set of dimensional reference information, not usable for more than one kind of calibration method.

Thus, it can be appreciated that there is a need for a better and more versatile calibration apparatus with a straightforward calibration approach that is particularly well suited for use with portable contour scanning apparatus, including dental intraoral imaging devices and stereo vision imaging.

SUMMARY

An aspect of this application is to advance the art of surface contour characterization by providing apparatus and methods that facilitate accurate calibration of a scanner that obtains images of a surface for contour analysis. Another aspect of this application is to address, in whole or in part, at least the foregoing and other deficiencies in the related art.

It is another aspect of this application to provide, in whole or in part, at least the advantages described herein.

Exemplary method and/or apparatus embodiments according to the application can address the need for improved calibration tools and calibration methods that allow advantages such as stereo vision and triangulation system calibration.

Exemplary method and/or apparatus embodiments according to the application can address the need for improved calibration tools and calibration methods that allow advantages such as calibration targets comprising active display devices.

Exemplary method and/or apparatus embodiments according to the application can address the need for improved calibration tools and calibration methods that allow advantages such as on-site recalibration of dental scanner systems by the end-user, for example.

According to an aspect of the present disclosure, there is provided a dental imaging apparatus for surface contour imaging of an object that can include a first sensing apparatus comprising at least one lens and a sensor that is configured to obtain one or more images of at least one surface position; and a calibration target comprising a spatial light modulator configured to form a prescribed set of calibration patterns, and whose display plane corresponds to the at least one surface position.

According to an aspect of the present disclosure, there is provided a method for calibration of a dental scanning device that can include (a) positioning a calibration target at a position relative to the dental scanning device, where the calibration target comprises a spatial light modulator configured to form a prescribed set of calibration patterns; (b) acquiring at least one image of the calibration target as the calibration target displays the prescribed set of calibration patterns that code the pixels of the spatial light modulator; (c) determining a coordinate correspondence between the 2D coordinates of the calibration target coordinate and 2D coordinates of the scanning device; and (d) determining calibration parameters for the dental scanning device according to the determined coordinate correspondence.

These objects are given only by way of illustrative example, and such objects may be exemplary of one or more embodiments of the present disclosure. Other desirable objectives and advantages inherently achieved by embodiments of the application may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DESCRIPTION OF EXEMPLARY EMBODIMENTS

The following is a description of exemplary embodiments, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

The term "exemplary" indicates that the description is used as an example, rather than implying that it is an ideal.

The term "in signal communication" as used in the application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional or volume images and a pixel for 2-dimensional (2-D) images. For the purposes of the description herein, the terms voxel and pixel can generally be considered equivalent, describing an image elemental datum that is capable of having a range of numerical values. Voxels and pixels have attributes of both spatial location and image data code value.

"Patterned light" is used to indicate light that has a predetermined spatial pattern, such that the light has one or more features such as one or more discernable parallel lines, curves, a grid or checkerboard pattern, or other features having areas of light separated by areas without illumination. In the context of the present disclosure, the phrases "patterned light" and "structured light" are considered to be equivalent, both used to identify the light that is projected onto the head of the patient in order to derive contour image data.

In the context of the present disclosure, the terms "viewer", "operator", "end-user", and "user" are considered to be equivalent and refer to the viewing practitioner, technician, or other person who views and manipulates a contour image that is formed from a combination of multiple structured light images on a display monitor or who performs a calibration procedure on equipment that obtains a contour image.

The term "set", as used herein, refers to a non-empty set, as the concept of a collection of one or more elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

A "viewer instruction", "operator instruction", or "operator command" can be obtained from explicit commands entered by the viewer or may be implicitly obtained or derived based on some other user action, such as making an equipment setting, for example. With respect to entries entered on an operator interface, such as an interface using a display monitor and keyboard, for example, the terms "command" and "instruction" may be used interchangeably to refer to an operator entry.

In the context of the present disclosure, a single projected line of light is considered a "one dimensional" pattern, since the line has an almost negligible width, such as when projected from a line laser, and has a length that is its predominant dimension. Two or more of such lines projected side by side, either simultaneously or in a scanned arrangement, provide a two-dimensional pattern. The terms "3-D model", "point cloud", "3-D surface", and "mesh" may be used synonymously in the context of the present disclosure. The dense point cloud is formed using techniques familiar to those skilled in the volume imaging arts for forming a point cloud and relates generally to methods that identify, from the point cloud, vertex points corresponding to surface features. The dense point cloud is thus generated using the reconstructed contour data from one or more reflectance images. Dense point cloud information serves as the basis for a polygon model at high density for the teeth and gum surface.

Stereo vision and triangulation imaging have been preferred methods in non-contact 3D surface measurement. The camera calibration plays a vital role in determining the accuracy of the 3D reconstruction in such stereo vision and triangulation imaging.

Two categories of camera calibration methods are popular today. The first category uses a planar or 3D rig calibration target with markers of known metric world coordinate. When a planar calibration target is used, the plane normal to the planar calibration target is aligned with the camera axis. Then, an accurate mechanical carrier moves the planar calibration target (remaining in the normal orientation to the camera axis) along to several discrete positions. Images are taken when the planar calibration target is static at these several discrete positions to form 3D marker coordinates. When a 3D rig calibration target is used, usually only one image is taken at each position. Then, image processing method such as corner detection is used to find the marker positions of the 3D rig calibration target in the image plane. The correspondence between the 3D marker positions' world coordinates and 2D image coordinates can be built for calibration. The second category uses calibration targets with planar checker board or planar markers with known world coordinates. Such a calibration target can be freely positioned, and images are taken of the calibration target at a number of positions and orientations. Images can then be fed into Zhang's calibration algorithm for calibration (Z. Zhang. Flexible Camera Calibration By Viewing a Plane From Unknown Orientations. *International Conference on Computer Vision* (*ICCV*'99), Corfu, Greece, pages 666-673, September 1999). The second category is popular because of its flexibility. However, the calibration accuracy in the second category is not satisfactory for applications with high accuracy requirements. Insufficient accuracy in the second category is attributed to facts including 1) high planarity target is difficult to produce, 2) the marker or the printed checker board corner(s) are unable to achieve high accuracy and/or linear alignment row by row and/or column by column, or 3) the markers or checker board corners are sparse, which makes it impossible for dense point to point correspondence within the whole plane, thus resulting in less accurate calibration.

Certain exemplary method and/or apparatus embodiments according to the application can provide a high accuracy calibration that uses active display calibration target devices like LCDs or spatial light modulators. Industrial LCD or even consumer level LCD can have a very high planarity of around 0.05 μm and very small pixel size of a few microns. Further, pixel linearity in rows and columns and consistency in spacing can also be extremely high in industrial LCD or consumer level LCD. Exemplary embodiments in the present application will yield better results using active display devices with a planarity better than approximately 10 μm. Industrial or consumer LCD can be controlled (e.g., programmed) to display selected or required calibration patterns. In selected exemplary method and/or apparatus embodiments, LCDs can display a series of predefined codeword patterns at a display plane, and images are captured by the scanner/camera (e.g., imager). By decoding codewords on the captured images, a one-to-one correspondence between image points on the imager and world points on the LCD plane (e.g., display plane) can be determined for a plurality of pixels or for every pixel. With dense, highly accurate correspondence points generated by the active display calibration target devices, calibration algorithms can produce high accuracy calibration parameters for the scanner/camera.

Figure 1:
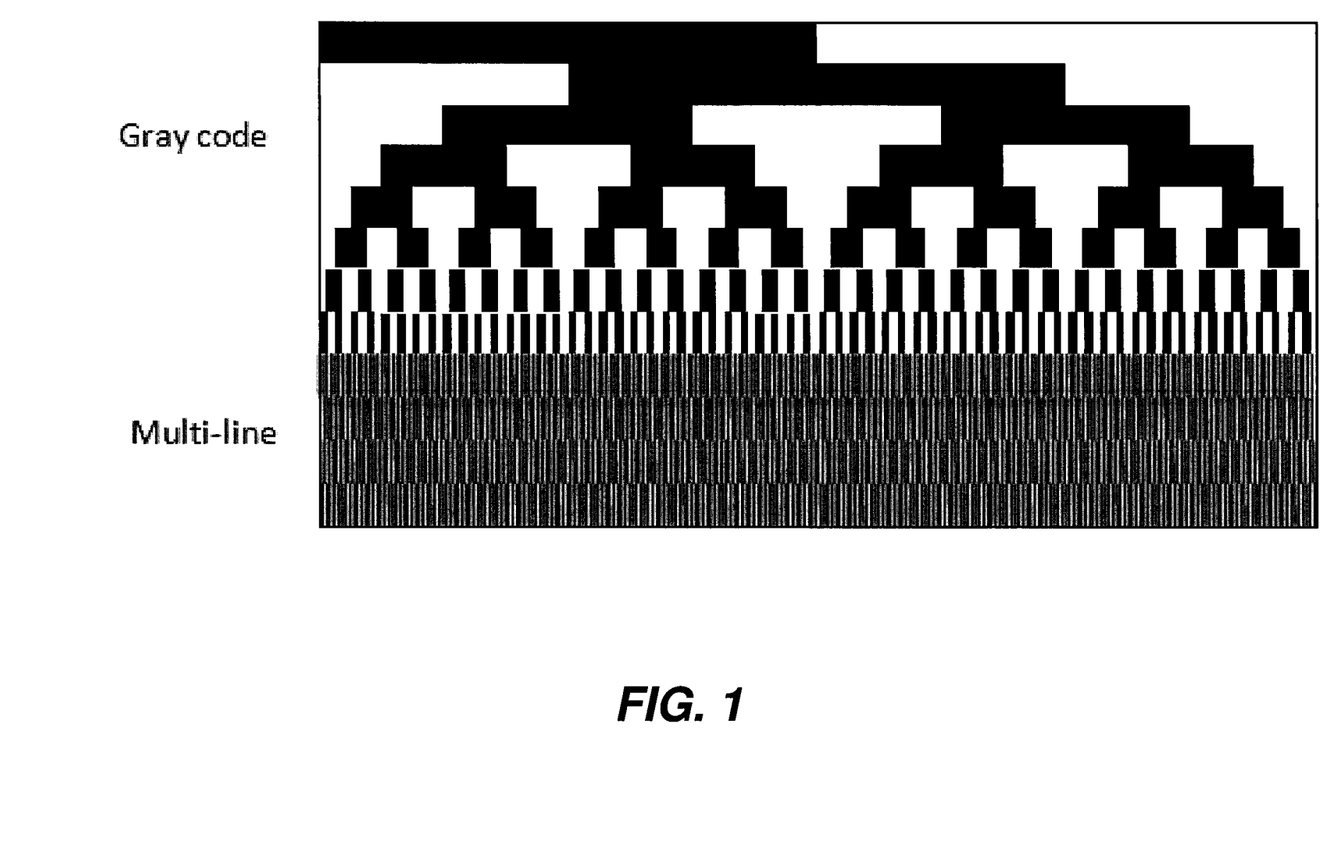
FIG. 1 is a diagram that shows an exemplary active display calibration target calibration pattern being a gray-code and multi-line combined codeword image.

Many pattern coding methods have been reported and are known to those skilled in the art of non-contact 3D surface measurement. Gray codes, phase shifting method, or combinations thereof are among the most popular pattern coding methods; however, embodiments of the application are not intended to be limited to such pattern coding methods. Further, phase calculation accuracy from captured calibration images can affect the correspondence accuracy. Thus, even when highly accurate target and dense target points are used, when the phase detection (of image points) is not accurately detected, the correspondence accuracy can be decreased or wouldn't be sufficient. To address such phase calculation concerns, one exemplary embodiment uses a coding method/apparatus that combines gray codes and line shifting, which can be based on sub-pixel peak detection to produce highly accurate image point location(s). The gray code divides the image into sub-regions. An "n" Gray code pattern will divide the target into 2^n sub-regions. An n-gray code is an n-bit codeword and needs n frames of images to encode the world. For example, 8-bit divide the target plane into 2^8=256 sub-regions. Within each sub-region shifting lines will give finer dividing resolution. If target plane has N=1024 horizontal pixels, then each sub-region has N/2^n=4 pixel width. To cover every pixel in this case, 4 line images with 256 vertical lines in each image will be used for multi-line shifting display. FIG. 1 is a diagram that shows the exemplary display on a spatial light modulator (e.g., LCD) forming a codeword image at a display plane (e.g., LCD plane) that codes horizontal LCD pixels. Furthermore, the same combined Gray-code and multiline pattern can be displayed in the orthogonal direction to form a codeword image that codes vertical LCD pixels. The set of calibration images thus includes vertical codeword and horizontal codeword. Alternatively, the set of calibration images can be a single codeword image that simultaneously codes horizontal and vertical LCD pixels. With the set of coded images, each pixel in LCD plane (e.g., display plane) can be uniquely defined.

Certain exemplary method and/or apparatus embodiments according to the application can be used for single camera imaging calibration. For single camera imaging, the following modeling matrices equations (1) and (2) can be used.

$$\lambda \tilde{m} = A[Rt]\tilde{M}, \quad \text{equation (1)}$$

$$\begin{pmatrix} x_d \\ y_d \end{pmatrix} = \begin{pmatrix} x_u(1 + k_1 r^2 + k_2 r^4 + \ldots) + (p_2(r^2 + 2x_u^2) + 2p_1 x_u y_u) \\ (1 + p_3 r^2 + p_4 r^4 + \ldots) \\ y_u(1 + k_1 r^2 + k_2 r^4 + \ldots) + (p_1(r^2 + 2y_u^2) + 2p_2 x_u y_u) \\ (1 + p_3 r^2 + p_4 r^4 + \ldots) \end{pmatrix}, \quad \text{equation (2)}$$

where $\tilde{M}=(X\ Y\ Z\ 1)^T$, is the homographic coordinate of the world points, $\tilde{m}=(u\ v\ 1)^T$, is the corresponding homographic coordinate in image plane. $A=[\alpha\ \gamma\ u_0;\ 0\ \beta\ v_0;\ 0\ 0\ 1]$ is the intrinsic matrix of the camera. $\alpha$ and $\beta$ are the nominal focus lengths along horizontal and vertical camera axis, respectively. $\gamma$ is the skew factor of image axis. $(u_0\ v_0)$ is the principal point in image plane. R and t are 3×3 rotation matrix with three unknown parameters and 3×1 translation matrix from world coordinate to camera coordinate, respectively. Equation (2) is a distortion modeling matrix with k radial distortion coefficients and p tangential distortion coefficients. Usually $k_1$, $k_2$, $k_3$, $p_1$ and $p_2$ are sufficient for modeling common image distortions. Matrices A, R and t and distortion coefficients $k_1, k_2, k_3, p_1, p_2$ are the unknowns to be determined from calibration, preferably by minimizing the function $$\sum_{i=1}^{n}\sum_{j=1}^{m}\left\|m_{ij}-\breve{m}(A,k_{1},k_{2},k_{3},p_{1},p_{2},R_{i},t_{i},M_{j})\right\|^{2},$$

where $\breve{m}(A, k_1, k_1, k_1, k_1, k_1, R_i, t_i, M_j)$ is the projection of $M_j$ according to equations (1) and (2). Additional details regarding use of equations (1) and (2), can be found in related art documents such as (i) Richard Hartley and Andrew Zisserman, "Multiple view geometry in computer vision". Cambridge University Press, March 2004; or (ii) Zhengyou Zhang, "A flexible new technique for camera calibration, "Pattern Analysis and Machine Intelligence, IEEE Transactions on, vol. 22, no. 11, pp. 1330, 1334, November 2000 (hereinafter Zhang).

Figure 2:
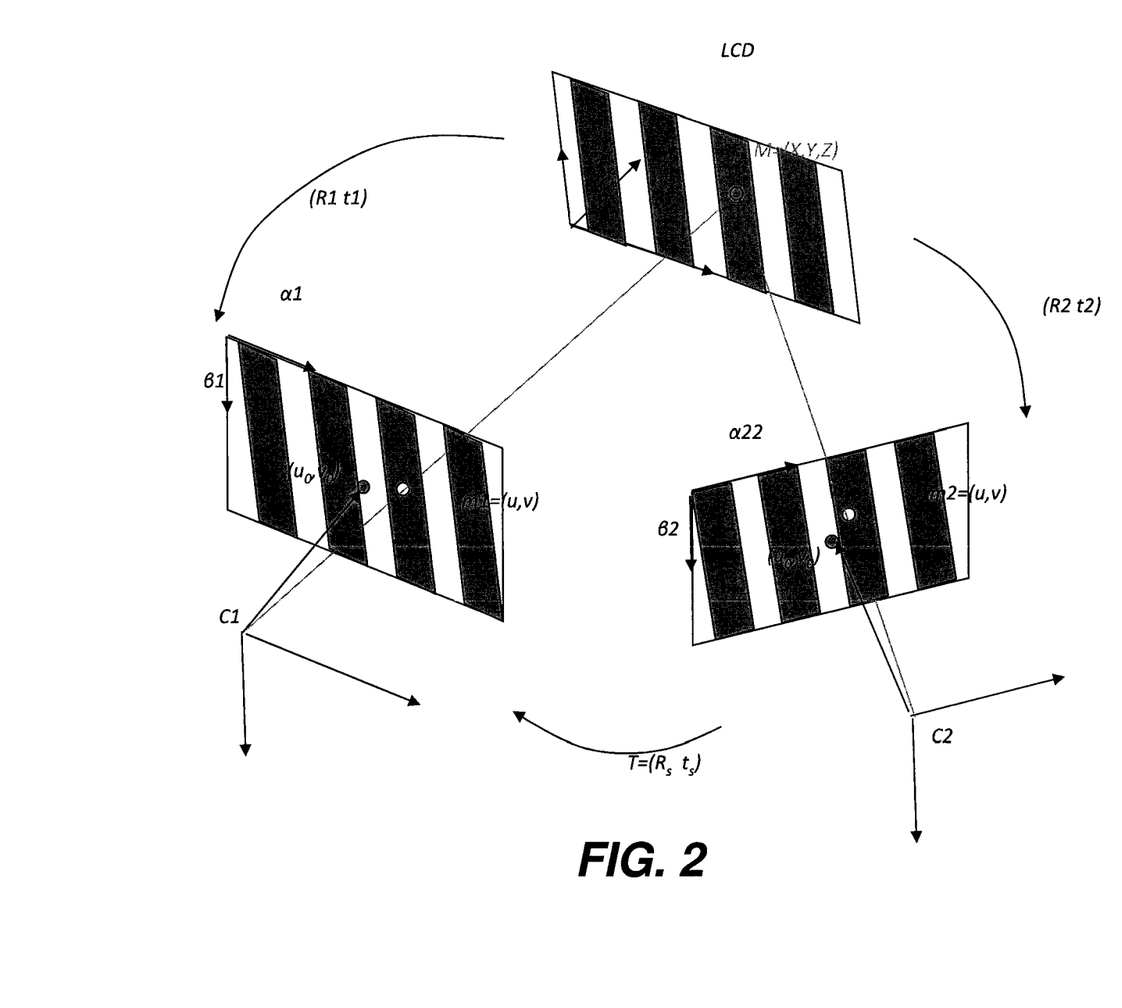
FIG. 2 is a diagram that shows an exemplary stereo vision calibration model according to embodiments of the application.

Certain exemplary method and/or apparatus embodiments according to the application can be used for stereo (or multi-view) scanner imaging calibration (e.g., using stereo or multi-view (three or more) scanner set-ups). With stereo scanner setup (or multi-view), two (or more) cameras can be configured with fixed rotation and translation among the cameras. FIG. 2 shows an exemplary embodiment of stereo vision setup and one LCD calibration target configuration position.

In one exemplary calibration apparatus embodiment, positions of camera C1 and camera C2 are fixed and the LCD calibration target starts static at one (e.g., first) arbitrary position. Camera C1 is directed toward the LCD calibration, target from an angle different from camera C2. At the first arbitrary position, the exemplary calibration apparatus can cause the set of codeword images to be displayed at the LCD calibration target and be captured by camera C1 and camera C2. After that, the exemplary calibration apparatus can change the LCD calibration target to another different (e.g., second) arbitrary position and preferably the same codeword images are displayed and again are captured by camera C1 and camera C2. This exemplary calibration apparatus can repeat the codeword display and capture process several times as LCD calibration target moves (automatically or manually) among a series or plurality of different arbitrary positions. Many different known coding methods can be used by this exemplary calibration apparatus to determine calibration parameters to calibrate camera C1 and camera C2 using the displayed codewords and captured images as long as precise image point position detection result therefrom. The determined calibration parameters are stored in the scanning device or used to replace old calibration data in the scanning device.

The LCD calibration target can be movably housed within a fixture, which is keyed to detachably couple to the cameras in a predetermined orientation. The fixture can provide an adjustment configured to change a distance and orientation between the LCD calibration target and the cameras. At the end of calibration procedure, the LCD calibration target can be detached from the exemplary calibration apparatus.

In one exemplary calibration method embodiment that can be implemented in the arrangement shown in FIG. 2, "n" positions of a LCD calibration target can be used. At each position, each camera captures 24 images of which 12 images are for vertical coding and 12 images are for horizontal coding. Algorithm is then used to detect peaks and then find codeword for each peak in each group of images from a position. Reading directly from LCD encoded codeword, the one-to-one correspondence between LCD coordinate and camera image peaks coordinate can be determined. Thus, a very dense one-to-one correspondence is built.

Measured data points can then be fed into Zhang's calibration algorithm to obtain calibration parameters. As shown in FIG. 2, camera C1 is directed toward the LCD calibration target from an angle different from camera C2. The two cameras preferably take images simultaneously and each camera is calibrated independently. One of the "n" LCD positions is preferably selected to be the reference. Obtained extrinsic matrix (R1 t1) and (R2 t2) can be used to calculate the stereo vision system's extrinsic matrix $T=(R_s, t_s)$, which describes the rotation and translation relationship between the two cameras. In one exemplary embodiment, at the end of calibration procedure, the LCD calibration target can be detached from the exemplary calibration apparatus.

For calibrating a single camera, the same process as described with respect to FIG. 2 is used, except that only one camera is involved. Single camera calibration obtains the intrinsic matrix and distortion coefficients for the camera.

Certain exemplary method and/or apparatus embodiments according to the application can be used in an active triangulation device to calibrate a projector with respect to a camera (e.g., a dental intraoral 3D scanner). In one exemplary calibration method embodiment, with an active display calibration target in one position, a projector in an active triangulation device can project fringe or structured illumination patterns onto the active display calibration target (e.g., a LCD) that is operating in a reflectance mode (i.e., display is disabled), and the fringe patterns reflected by the active display calibration target are captured in images by a camera/sensor in the active triangulation device. Before or after that, the active display calibration target displays a single (or series of) calibration coding pattern (as described herein). The displayed calibration coding pattern is captured by the camera in the active triangulation device. Thus for each camera sensor pixel, there are at least two coding words decoded from each of the projector fringe patterns and active display calibration target calibration coding pattern, providing dense matching of the active display calibration target pixels and the projector pixels. The above-described procedure can be repeated with the active display calibration target in multiple positions and orientations. Accordingly, the projector in the active triangulation device can be calibrated using Zhang's calibration method where the projector is treated like a second camera.

Figure 3:
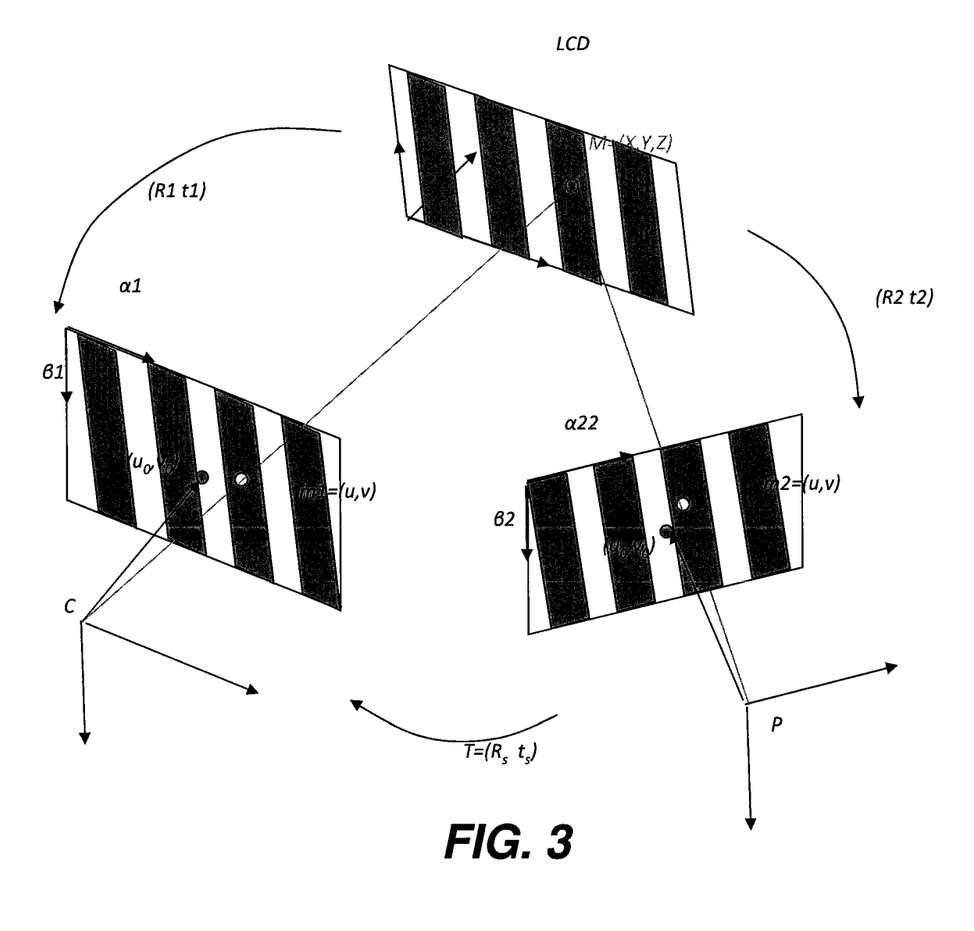
FIG. 3 is a diagram that shows an exemplary projector calibration model according to embodiments of the application.

FIG. 3 shows an exemplary embodiment of a projector and camera configuration using one LCD calibration target in one pose according to the application. As shown in FIG. 3, C is the camera center, and P is the projector center. When calibrating the projector, first, the LCD calibration target is turned off, and the projector projects patterns on the LCD calibration target; reflected projector patterns are then captured by the camera. Second, the projector is turned off, and the LCD calibration target displays its coding patterns (e.g., as shown in FIG. 1), and the coding patterns are also captured by the camera. Thus for each LCD calibration target pose, the camera captures two sets of patterns, namely the reflected projector patterns and the coding patterns. After decoding, the image plane has at least two sets of densely distributed coding words to provide matching between projector and the LCD calibration target, by calculating the "image" of LCD calibration target pixel on the projector plane. One way of calculating the "image" is by locally interpolating the LCD target's pixel position at projector plane via the relation between this pixel and its neighbor at camera plane. The above-described procedure can be repeated with the active display calibration target in multiple poses. From the correspondences between the decoded patterns, Zhang's method can be used to calibrate the projector like a second camera. Finally, captured patterns of the LCD calibration target can be used to calibrate the camera C. With these calibrations, the system extrinsic calibration parameter T could be obtained easily.

Exemplary method and/or apparatus embodiments according to the application have various advantages. One advantage of the exemplary active display calibration target embodiments is the flexibility to generate any pattern for calibration, such as but not limited to checker board pattern for common calibration, coded images for dense correspondence points and/or high precision calibration. Exemplary method and/or apparatus active display calibration target embodiments can be used for single camera calibration, stereo vision calibration, three or more multi-view vision calibration, and/or projector-camera calibration. Certain exemplary method and/or apparatus embodiments can be used together with a highly accurate mechanical/electromechanical carrier. One exemplary active display calibration target embodiment can be formed with high quality, dense rigid 3D points like those used in the first category calibration. Another exemplary active display calibration target embodiment can implement high precision calibration of modeling parameters that can be used to give high precision distortion calibration because of the dense point correspondence provided.

Figure 4:
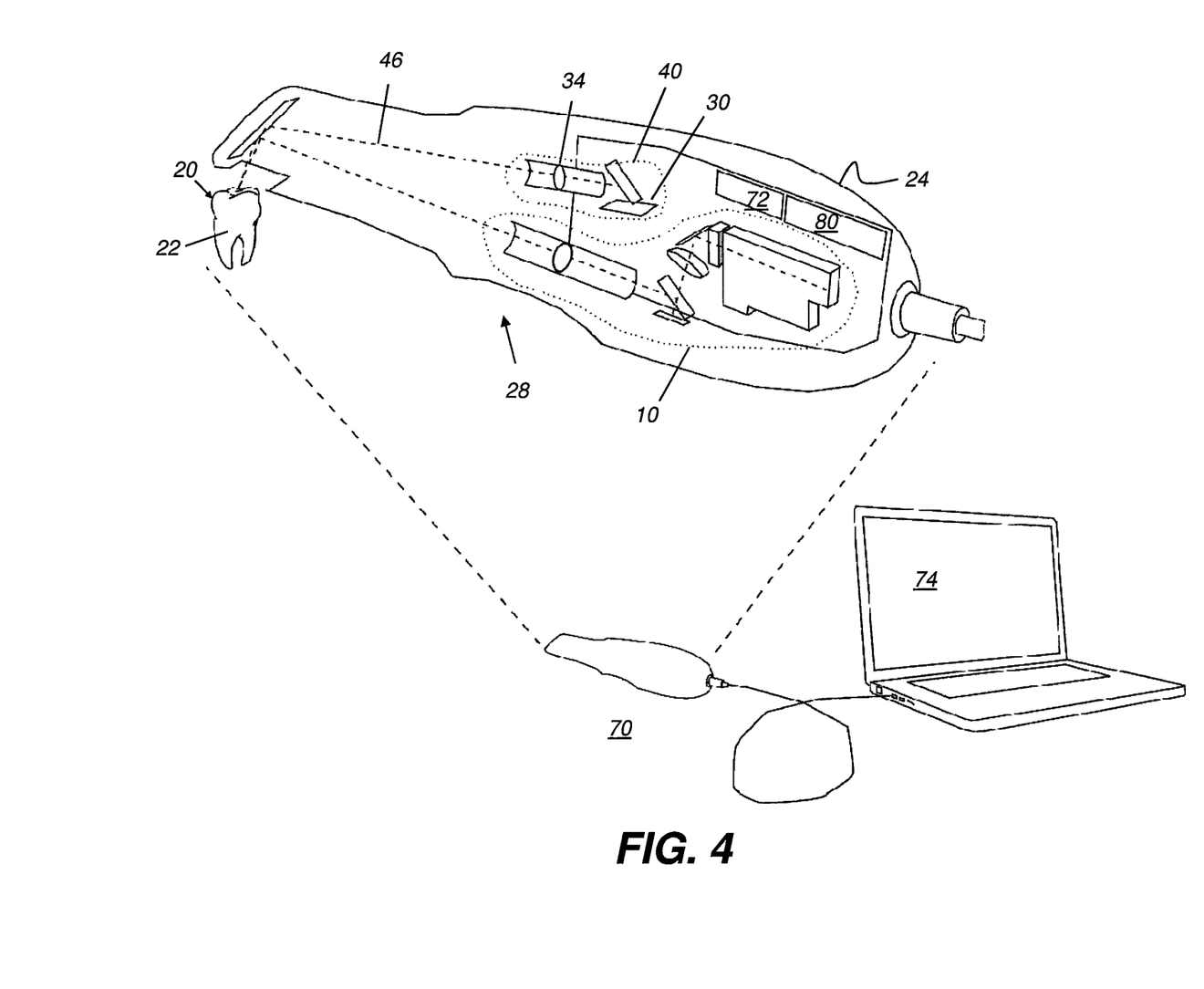
FIG. 4 is a schematic diagram that shows components of an imaging apparatus for surface contour imaging of a patient's teeth and related structures.

FIG. 4 is a schematic diagram showing an imaging apparatus 70 that operates as a camera 24 for image capture as well as a scanner 28 for projecting and imaging to characterize surface contour using structured light patterns 46, and that can be calibrated according to the presently disclosed method. Imaging apparatus 70 can be a handheld device (as shown) or a desktop scanner; it uses a camera 24 for image acquisition for both contour scanning and image capture functions according to an embodiment of the present disclosure. A control logic processor 80, or other type of computer that may be part of camera 24, controls the operation of an illumination array 10 that generates the structured light and directs the light toward a surface position and controls operation of an imaging sensor array 30. Image data from surface 20, such as from a tooth 22, is obtained from imaging sensor array 30 and stored in a memory 72. Imaging sensor array 30 is part of a sensing apparatus 40 that includes an objective lens 34 and associated elements for acquiring image content. Control logic processor 80, in signal communication with camera 24 components that acquire the image, processes the received image data and stores the mapping in memory 72. The resulting image from memory 72 is then optionally rendered and displayed on a display 74. Memory 72 may also include a display buffer.

In structured light imaging, a pattern of lines is projected from illumination array 10 toward the surface of an object from a given angle. The projected pattern from the illuminated surface position is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of structured light imaging, used in order to complete the contour mapping of the surface and to increase overall resolution in the contour image.

Figure 5:
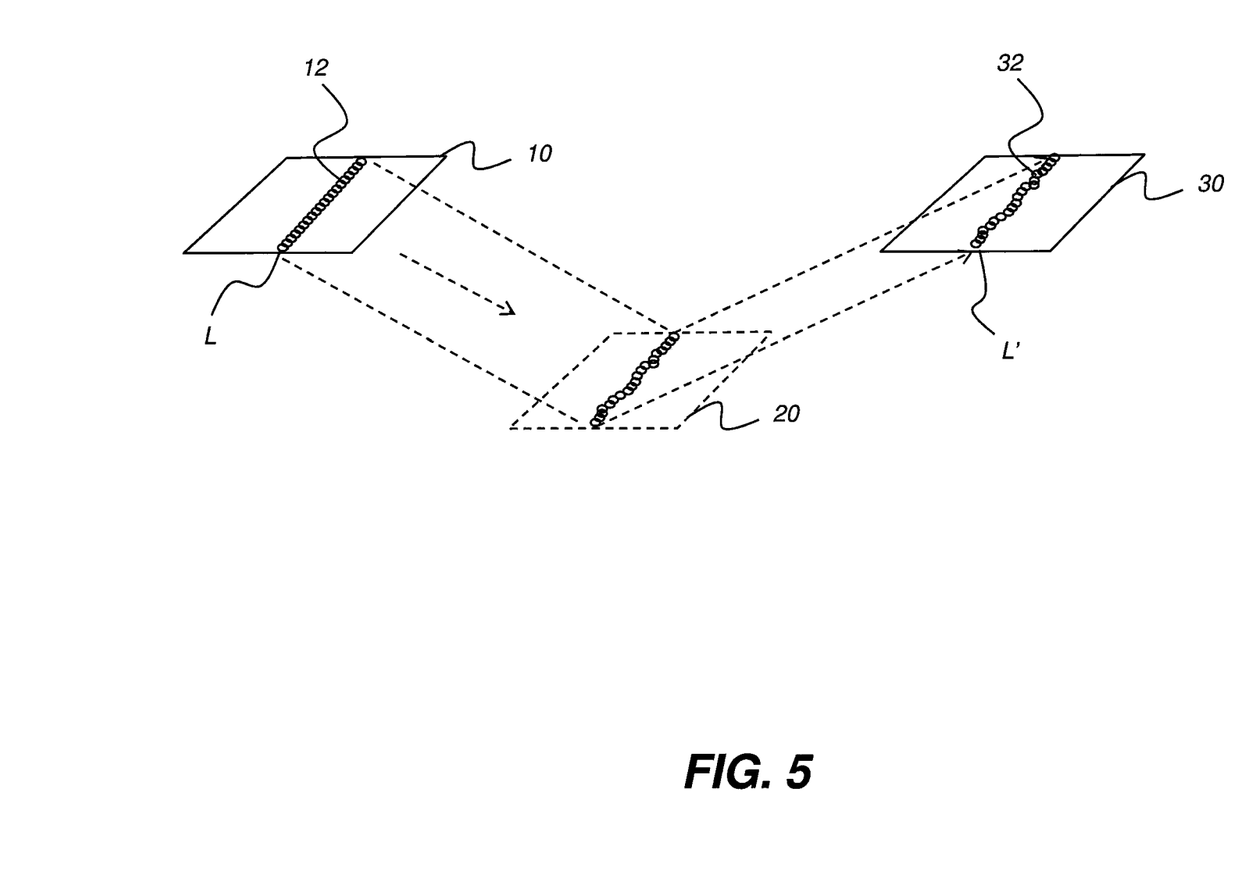
FIG. 5 shows schematically how patterned light is used for obtaining surface contour information using a handheld camera or other portable imaging device.

The schematic diagram of FIG. 5 shows, with the example of a single line of light L, how patterned light is used for obtaining surface contour information by a scanner using a handheld camera or other portable imaging device. A mapping is obtained as an illumination array 10 directs a pattern of light onto a surface 20 and a corresponding image of a line L' is formed on an imaging sensor array 30. Each pixel 32 on imaging sensor array 30 maps to a corresponding pixel 12 on illumination array 10 according to modulation by surface 20. Shifts in pixel position, as represented in FIG. 5, yield useful information about the contour of surface 20. It can be appreciated that the basic pattern shown in FIG. 5 can be implemented in a number of ways, using a variety of illumination sources and sequences and using one or more different types of sensor arrays 30. Illumination array 10 can utilize any of a number of types of arrays used for light modulation, such as a liquid crystal array or digital micromirror array, such as that provided using the Digital Light Processor or DLP device from Texas Instruments, Dallas, Tex. This type of spatial light modulator is used in the illumination path to change the light pattern as needed for the mapping sequence.

By projecting and capturing images that show structured light patterns that duplicate the arrangement shown in FIG. 4 multiple times, the image of the contour line on the camera simultaneously locates a number of surface points of the imaged object. This can speed the process of gathering many sample points, while the plane of light (and usually also the receiving camera) is laterally moved in order to "paint" some or all of the exterior surface of the object with the plane of light.

Multiple structured light patterns can be projected and analyzed together for a number of reasons, including to increase the density of lines for additional reconstructed points and to detect and/or correct incompatible line sequences. Use of multiple structured light patterns is described in commonly assigned U.S. Patent Application Publications No. 2013/0120532 and No. 2013/0120533, both entitled "3D INTRAORAL MEASUREMENTS USING OPTICAL MULTILINE METHOD" and incorporated herein in their entirety.

Figure 6:
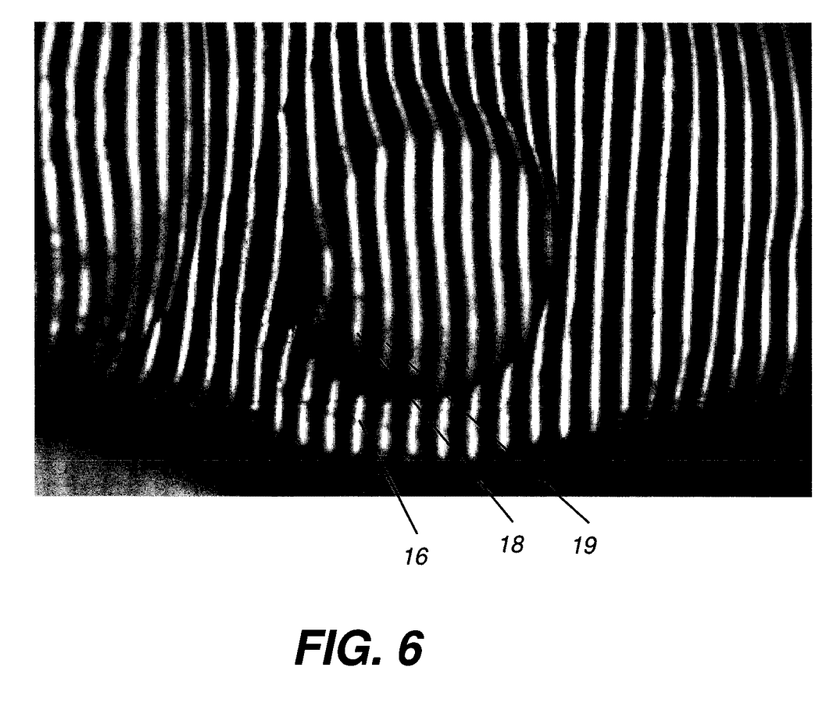
FIG. 6 shows an example of dental surface imaging using a pattern with multiple lines of light.

FIG. 6 shows surface imaging using a pattern with multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 6, for example, it can be difficult over portions of the surface to determine whether line segment 16 is from the same line of illumination as line segment 18 or adjacent line segment 19.

By knowing the instantaneous position of the camera and the instantaneous position of the line of light within an object-relative coordinate system when the image was acquired, a computer and software can use triangulation methods to compute the coordinates of numerous illuminated surface points. As the plane is moved to intersect eventually with some or all of the surface of the object, the coordinates of an increasing number of points are accumulated. As a result of this image acquisition, a point cloud of vertex points or vertices can be identified and used to represent the extent of a surface within a volume. The points in the point cloud then represent actual, measured points on the three dimensional surface of an object.

Calibration-related errors can be particularly troublesome, complicating and even compromising accurate construction of a point cloud that represents the surface contour.

Certain exemplary method and/or apparatus embodiments according to the application can be implemented in the imaging apparatus 70 shown in FIG. 4.

In general, calibration is performed using a calibration target and requires some type of reference surface. In order to provide the needed quality, the overall precision of the calibration target must significantly exceed the desired precision of the scanner. As a rule of thumb, a precision of at least about 10 times better than the desired precision of the scanner is considered acceptable. For an intraoral scanner, achieving at least 50 micron precision thus means fabricating a calibration target that is accurate to within 5 microns. This can be a considerable challenge, even out of range for many manufacturing environments. Certain exemplary method and/or apparatus embodiments according to the application can meet the calibration requirements of such intraoral scanners.

Exemplary method and/or apparatus embodiments according to the application can provide a calibration target that can be used by the end-user (e.g., dentist, dental technician) of an intraoral scanner apparatus for in-house validation of calibration of the intraoral scanner apparatus and/or to provide data that can be used for calibration readjustment. Advantageously, calibration target embodiments can be easily fitted to an intraoral scanner. Out-of-calibration errors that are detected can be corrected automatically by the scanning logic. Such scanning logic can be located in calibration target embodiments, intraoral scanners or a remote processor/computer in signal communication with one of the same.

As can be appreciated by those skilled in the image processing arts, a computer program for acquiring and processing calibration measurements in an embodiment of the present disclosure can be utilized by a suitable, general-purpose computer system, such as a personal computer or workstation that acts as an image processor, when provided with a suitable software program so that the processor operates to acquire, process, and display data as described herein. Many other types of computer systems architectures can be used to execute the computer program of the present disclosure, including an arrangement of networked processors, for example.

The computer program for performing the method of the present disclosure may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present disclosure may make use of various imaging and related data manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing and calibration arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention has been described in detail, and may have been described with particular reference to a suitable or presently preferred embodiment, but it will be understood that variations and modifications can be effected within the spirit and scope of the invention. The presently disclosed exemplary embodiments are therefore considered in all respects to be illustrative and not restrictive.

In this document, the terms "a" or "an" are used, as is common in patent documents, to include one or more than one, independent of any other instances or usages of "at least one" or "one or more". In this document, the term "or" is used to refer to a nonexclusive or, such that "A or B" includes "A but not B", "B but not A", and "A and B", unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

What is claimed is:

1. A dental imaging apparatus for surface contour imaging of an object, the dental imaging apparatus comprising:
   a calibration target comprising:
      a spatial light modulator configured to form a prescribed set of calibration patterns that are displayed at display of the calibration target;
   an intraoral apparatus for surface contour imaging of dentition comprising:
      an illumination array configured to direct one or more illumination patterns toward the display of the calibration target; and
      a sensor array including at least one lens and a sensor that is configured to obtain one or more images of the display of the calibration target;
   where the sensor obtains at least one image of the prescribed set of calibration patterns displayed at the display of the calibration target, and where the sensor obtains at least one image of the illumination patterns reflected by the display of the calibration target, and
   where illumination patterns are directed before or after the displaying of the prescribed set of calibration patterns, and
   where the obtained images of the illumination patterns and calibration patterns by the sensor are decoded by a control logic processor coupled to the calibration target or the intraoral apparatus to determine a one-to-one correspondence between the image points on an illumination apparatus of the illumination array and points on the display of the calibration target to re-calibrate the sensor.

* * * * *

UNITED STATES PATENT AND TRADEMARK OFFICE
CERTIFICATE OF CORRECTION

| | | |
|---|---|---|
| PATENT NO. | : 11,484,282 B2 | Page 1 of 1 |
| APPLICATION NO. | : 16/060853 | |
| DATED | : November 1, 2022 | |
| INVENTOR(S) | : Victor C. Wong and Chuanmao Fan | |

It is certified that error appears in the above-identified patent and that said Letters Patent is hereby corrected as shown below:

On the Title Page

Item (72) Inventors: "Victor Wong, Pittsford, NY (US); Chuanmao Fan, Rochester, NY (US)" should read --Victor C. Wong, Pittsford, NY (US); Chuanmao Fan, Rochester, NY (US)--

Signed and Sealed this
First Day of August, 2023

Katherine Kelly Vidal
*Director of the United States Patent and Trademark Office*